United States Patent [19]

Lukas et al.

[11] 4,031,152

[45] June 21, 1977

[54] PREPARATION OF DERIVATIVES OF CYCLOBUTANE AND CYCLOBUTENE

[75] Inventors: Joachim H. Lukas; Frank Baardman; Adriaan P. Kouwenhoven, all of Amsterdam, Netherlands

[73] Assignee: Shell Oil Company, Houston, Tex.

[22] Filed: Dec. 22, 1975

[21] Appl. No.: 643,419

Related U.S. Application Data

[62] Division of Ser. No. 468,949, May 10, 1974, Pat. No. 3,965,204.

[30] Foreign Application Priority Data

May 10, 1973 United Kingdom ............. 22362/73

[52] U.S. Cl. .................... 260/666 A; 260/666 PY
[51] Int. Cl.$^2$ .................... C07C 3/03; C07C 13/06
[58] Field of Search ................. 260/666 A, 666 PY

[56] References Cited

UNITED STATES PATENTS

| | | | |
|---|---|---|---|
| 2,957,035 | 10/1960 | Benson | 260/666 A |
| 3,258,501 | 6/1966 | Cannell | 260/666 PY |
| 3,347,875 | 10/1967 | Foster et al. | 260/666 PY |

*Primary Examiner*—Delbert E. Gantz
*Assistant Examiner*—C. E. Spresser

[57] ABSTRACT

Preparation of alkylidenecyclobutane derivatives and of cyclobutene derivatives by contacting a (cyclo)alkene with an allene or with a 1-alkyne in the liquid phase in the presence of a dissolved Lewis acid derived from an element of Group III A of the Periodic Table of the Elements, titanium, tin, antimony, tantalum, rhenium, iron, or zinc.

12 Claims, No Drawings

PREPARATION OF DERIVATIVES OF CYCLOBUTANE AND CYCLOBUTENE

This is a division of application Ser. No. 468,949, filed May 10, 1974, now U.S. Pat. No. 3,965,204.

BACKGROUND OF THE INVENTION

It is known that certain olefinically unsaturated compounds containing an activating or polar group may undergo thermal cyclo-addition reactions with allene to form correspondingly substituted methylene cyclobutene derivatives, for example, the known reaction of acrylonitrile, methyl acrylate, acrylic acid and styrene with allene to form the corresponding cyano-, carbomethoxy-, carboxy- and phenyl-substituted methylene cyclobutanes. It also is known that allene will dimerize thermally to yield a dimethylene cyclobutane.

The occurrence of these reactions appears to depend upon the activating effects of the polar substituents, upon the presence of the aromatic phenyl group in the case of styrene, or upon the active nature of the double bonds in the case of allene itself. We are not aware of any instance in which allene or a homolog of allene has been successfully reacted with an olefin hydrocarbon containing four or more carbon atoms, that is devoid of such activating groups. Indeed, it appears that simple thermal cyclo-addition of allene to alkenes is not possible to achieve, products of cyclodimerization or other polymerization of the individual reactants being exclusively formed.

SUMMARY OF THE INVENTION

It now has been discovered that allene hydrocarbons, i.e., allene and higher hydrocarbons that contain the >C=C=C< grouping may be caused to undergo cyclo-addition to simple mono-olefins having a primary or secondary alkyl group substituted on each of the olefin carbon atoms, provided that the reaction is conducted in the presence of certain catalysts, namely, catalysts of the type that are known in the art as Lewis acids and derived from an element of Group III A of the Periodic Table of the Elements, titanium, tin, antimony, tantalum, rhenium, iron or zinc. It has been further discovered that this new reaction may be extended to that of such simple mon-olefins with acetylene hydrocarbons, in lieu of allene and its higher homologs, that have a hydrocarbon group directly substituted on one, and only one, of the acetylene carbon atoms. In this instance, the reactivity of the acetylenic linkage appears to be comparable to that of the allene structure. The products of the cyclo-addition reaction contain the cyclobutene structure, in contrast to the methylene-substituted butanes that are obtained when an allenic hydrocarbon is employed.

The process of this invention has been found to be generally applicable to simple mono-olefins (including cyclo-olefins) having a primary or secondary alkyl group substituted on each terminal carbon atom of the olefin or >C=C< group and wherein each of the remaining two valences is satisfied by bonding to a hydrogen atom; or to simple mono-olefins having two primary or secondary alkyl group substituted on one terminal carbon atom of the olefin or >C=C< group and wherein the other two valences are each satisfied by bonding to a hydrogen atom; or to cyclo-olefins where an alkylene group together with the >C=C< group forms a cyclo-olefin ring having 4, 5 or 7 or more than 7 carbon-atoms in the ring and wherein the other two valences of this >C=C< group are satisfied by primary or secondary alkyl groups; or to 2a, 3, 6, 6a tetrahydro-2-methylene cycloalkacyclohexene; ring or to olefins wherein one terminal carbon atom of the olefin or >C=C< group forms a part of a cyclobutane ring and wherein the other two valences are satisfied by one or more primary or secondary alkyl groups.

The allene hydrocarbon reactant may be allene itself or simple allene derivatives having one or more hydrogen atoms or hydrocarbyl groups substituted on each terminal carbon atom of the allene skeleton or >C=C=C< group.

The process when extended to alkyne reactants employee simple alkynes wherein one terminal carbon atom of the alkyne or HC≡C— group is substituted by a hydrocarbyl group.

All of the reactants, i.e. olefins, allene and alkynes are free of polar or activating substitutions.

More particularly, the invention relates to a process for the preparation of alkylidenecyclobutane derivatives having the general formulas

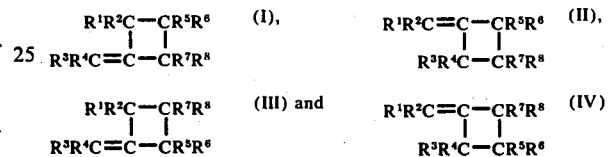

and of cyclobutene derivatives having the general formulas

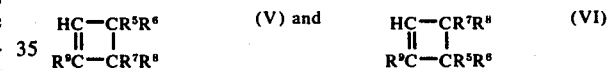

in which formulas I–VI $R^1$, $R^2$, $R^3$ and $R^4$ each individually represent a hydrogen atom or a hydrocarbyl group, $R^5$ and $R^8$ a primary or secondary hydrocarbyl group, $R^6$ and $R^7$ a hydrogen atom, a primary or secondary hydrocarbyl group, $R^9$ a hydrocarbyl group and $R^5$ and $R^6$ each individually may represent a hydrogen atom when $R^7$ represents a primary or secondary hydrocarbyl group having at least 2 carbon atoms and $R^8$ a primary or secondary hydrocarbyl group, while $R^6$ and $R^7$ together may form part of a cycloaliphatic ring having 4, 5, 7 or more than 7 carbon atoms or a 2a, 3,6,6a-tetrahydrocy-clohexene ring, or, alternatively, while $R^5$ and $R^6$, or $R^7$ and $R^8$ in the formulas I, II, III and IV, together with the carbon atom to which they are bound, may form a cyclobutane ring. Cyclobutene derivatives having the general formulas V and VI are novel compounds.

Alkylidenecyclobutane derivatives having the general formulas I-VI are suitable precursors of cyclopropanecarboxylic acids which in turn are suitable pyrethrin precursors. Substituted cyclopropanecarboxylic acid esters are especially suitable as insecticides, because they combine a high insecticidal activity with a low mammalian toxicity.

It is an object of the present invention to make the alkylidenecyclobutane derivatives having the general formulas I-IV and the cyclobutene derivatives having the general formulas V and VI easily accessible.

The invention may be defined as relating to a process for the preparation of alkylidenecyclobutane derivatives having the general formulas

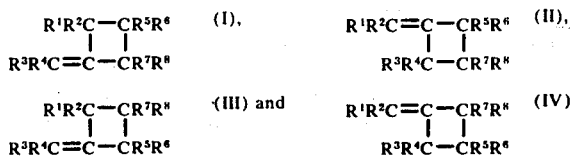

and of cyclobutene derivatives having the general formulas

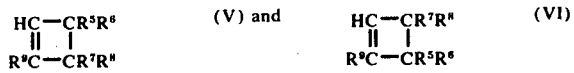

in which formulas I–IV $R^1$, $R^2$, $R^3$ and $R^4$ each individually represent a hydrogen atom or a hydrocarbyl group, $R^5$ and $R^8$ a primary or secondary alkyl group, $R^6$ and $R^7$ a hydrogen atom, a primary or secondary hydrocarbyl group, $R^9$ a hydrocarbyl group and $R^5$ and $R^6$ each individually may represent a hydrogen atom when $R^7$ represents a primary or secondary hydrocarbyl group having at least 2 carbon atoms and $R^8$ a primary or secondary hydrocarbyl group, while $R^6$ and $R^7$ together may form part of a cycloaliphatic ring having 4, 5, 7 or more than 7 carbon atoms or a 2a, 3, 6, 6a-tetrahydro-2-methylene cycloalkacyclohexene ring, or alternatively, while $R^5$ and $R^6$, or $R^7$ and $R^8$ in the formulas I, II, III and IV together with the carbon atom to which they are bound, may form a cyclobutane ring, which process comprises contacting a (cyclo)alkene having the general formula

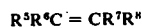 (VII)

with an allene having the general formula $R^1R^2C = C = CR^3R^4$ (VIII)

or with a 1-alkyne having the general formula

 (IX), $R^1$, $R^2$, $R^3$, $R^4$, $R^5$, $R^6$, $R^7$, $R^8$ and $R^9$ in the formulas VII–IX having the same meanings as in the formulas I–VI, in the liquid phase in the presence of a dissolved Lewis acid derived from an element of Group IIIA of the Periodic Table of the Elements, titanium, tin, antimony, tantalum, rhenium, iron or zinc.

The four alkylidenecyclobutane derivatives having the general formulas I–IV may be formed with equal or different selectivities. The choice of the compounds VII and VIII influences the selectivity to each of the alkylidenecyclobutane derivatives having the general formulas I–IV. The selectivity to a compound formed is defined as the molar percentage this compound constitutes of all compounds formed by the conversion of the starting compounds. When $R^5=R^7$ and $R^6=R^8$ not more than two different alkylidenecyclobutane derivatives can be formed. These two derivatives may each be formed with a selectivity of 50 or about 50%, but is is possible that one of the two derivatives is preferentially formed, for example with a selectivity of 90–100%, depending on the choice of the compounds VII and VIII. When, moreover, $R^1=R^3$ and $R^2=R^4$, only one alkylidenecyclobutane derivative can be formed. When $R^5=R^6=H$ and $R^7$ represents a primary or secondary hydrocarbyl group having at least two carbon atoms and $R^8$ a primary or secondary hydrocarbyl group, not less than two different alkylidenecyclobutane derivatives having the general formulas I–IV can be formed. The cyclobutene derivatives having the general formulas V and VI may each be formed with a selectivity of 50 or about 50%, but it is possible that one of the two derivatives is preferentially formed, for example with a selectivity of 90–100%, depending on the choice of the compounds VII and IX i.e. such that not more than one cyclobutene derivative having the general formula V or VI can be formed with $R^5=R^7$ and $R^6=R^8$.

The above-mentioned hydrocarbyl groups may be alkyl, cycloalkyl, or aryl group; substitution of these groups is not excluded providing the substitutions are non-polar groups. The number of carbon atoms of these three groups is not critical, except for $R^7$ as indicated above. The alkyl groups may be primary, secondary or tertiary that is straight or branched and may contain up to, for example, 20 carbon atoms. Examples of alkyl groups which may be used are methyl, ethyl, propyl, i-propyl, butyl, sec-butyl and, for $R^1$, $R^2$, $R^3$, $R^4$ and $R^9$, tert-butyl groups; examples or hydrocarbyl-substituted alkyl groups are benzyl, phenethyl and trityl groups. Examples of aryl groups are phenyl and naphthyl groups and examples of hydrocarbyl-substituted aryl groups are tolyl and xylyl groups. The compounds having the general formulas I–IV are together obtained in a very high yield, usually of more than 90%, when as compound having the general formula VII a tetrahydrocarbylethene, in particular a tetraalkylethene is used. Excellent yields have been obtained with 2,3-dimethyl-2-butene and 2,3,4-trimethyl-2-pentene. Other examples of alkenes having the general formula VII are 2-butene, 2-pentene, 2-hexene, 3-hexene, 2-heptene, 3-heptene, 2-methyl-2-butene, 3-methyl-2-pentene, 3-methyl-3-hexene and 2,4-dimethyl-3-hexene. Isobutene is excluded because it polymerizes under the conditions of the process of the invention.

Cis- and trans-alkenes may be used as starting alkenes. The alkenes may have two or more double bonds per molecule, but these double bonds should be non-conjugated.

Preferably, in the allene having the general formula VIII $R^1$, $R^2$, $R^3$ and $R^4$ each individually represent a hydrogen atom or an alkyl group. Specific examples of allenes are allene itself, 1-methylallene, 1,1-dimethylallene, 1,1-diethylallene, 1,1-di-n-nonylallene, 1-n-dodecylallene and 1-phenylallene. The compounds having the general formulas I–IV are together obtained in a very good yield when allene itself and methylallene are applied.

Preferably, in the 1-alkyne having the general formula IX $R^9$ represents an alkyl group. Specific examples of 1-alkynes are propyne, 1-butyne, 1-pentyne, 1-hexyne, 1-heptyne, 1-dodecyne, 2-methyl-1-pentyne, phenylethyne and 3-phenyl-1-propyne.

The cycloalkenes which are used according to the invention react with the allenes having the general formula VIII with formation of alkylidenecyclobutacycloaliphatic compounds and with the 1-alkynes having the general formula IX with formation of cyclobutacyclo-aliphatic compounds having a double bond between the carbon atoms in the first and second positions in the $C_4$ ring. The cycloalkenes may have two or more double bonds per molecule, but these double bonds should be non-conjugated. Examples of suitable cycloalkenes are cyclobutene, cyclopentene, 1,4-cyclohexadiene, 1,4-cycloheptadiene, 1,5-cyclooctadiene and 1,5,9-cyclododecatriene.

Two or more (cyclo) alkenes having the general formula VII, two or more allenes having the general formula VIII and two or more 1-alkynes having the general formula IX may be used as starting materials.

As the alkylidenecyclobutane derivatives formed are usually capable of reacting in the same way with the starting allene with the formation of alkylidenespiro hydrocarbons and even of polyspiro hydrocarbons, and the cyclobutene derivatives in the same way with the starting 1-alkyne with the formation of polycyclic hydrocarbons, it is recommended that for the preparation of compounds having the general formulas I–IV and V–VI relatively low molar ratios allene:alkene and alkyne:alkene, respectively, be applied of less than, for example, 1.5. Very good results are usually obtained when this molar ratio is between 0.1 and 1.5. The said two molar ratios may of course be chosen relatively high, higher than for example 1.5, if it is desired to prepare these alkylidenespiro hydrocarbons and polycyclic hydrocarbons. The latter two types of hydrocarbons are novel compounds. The bicyclic hydrocarbons among these polycyclic hydrocarbons have the following general formulas:

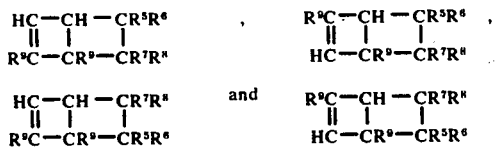

in which formulas $R^5$ and $R^8$ each represent a primary or secondary alkyl group, $R^6$ and $R^7$ a hydrogen atom, a primary or secondary hydrocarbyl group, $R^9$ a hydrocarbyl group and $R^5$ and $R^6$ each individually may represent a hydrogen atom when $R^7$ represents a primary or secondary hydrocarbyl group having at least 2 carbon atoms and $R^8$ a primary or secondary hydrocarbyl group.

Examples of Lewis acids — being compounds which receive one or more pairs of electrons to form a coordinate covalent bond — are boron trichloride, boron tribromide, aluminium chloride, aluminium bromide, gallium trichloride, gallium tribromide, titanium tetrachloride, titanium tetrabromide, stannic chloride, stannic bromide, antimony pentachloride, tantalum pentachloride, rhenium pentachloride and ferric chloride. Other examples of Lewis acids are metal alkyls and metal alkoxides. Examples of metals wherefrom these Lewis acids can be derived are zinc, boron, aluminium, gallium, indium and thallium. Organometal compounds derived from the zinc and aluminium are particularly suitable, those derived from aluminium being preferred.

As examples of suitable organometal compounds may be mentioned ethylzinc chloride, monoalkylaluminium dihalides such as ethylaluminium dichloride, ethylaluminium dibromide, propylaluminium dichloride, isobutylaluminium dichloride, ethylaluminium di-iodide; arylaluminium dihalides, such as phenylaluminium dichloride, phenylaluminium dibromide, phenylaluminium di-iodide, tolylaluminium dichloride, tolylaluminium dibromide, tolylaluminium di-iodide.

Alkylhaloaluminium compounds, such as dialkylaluminium monohalides, and in particular monoalkylaluminium dihalides are preferred. In the group of the alkylhaloaluminium compounds alkylchloroaluminium compounds, in particular ethylaluminium dichloride, are preferred.

Mixtures of aluminium compounds with one or more aluminiumcarbon bonds may also be used, for example, mixtures of dialkylaluminium halides and alkylaluminium dihalides, such as ethylaluminium sesquichloride and bromide.

The reaction can be carried out in the presence or in the absence of a solvent. In the latter case the Lewis acid is dissolved in the unsaturated starting material to be reacted. However, preferably a solvent is used which should not readily react with the Lewis acid or the unsaturated compounds present. Examples of suitable solvents are aliphatic, cycloaliphatic and aromatic hydrocarbons, such as pentane, hexane, petroleum ether, decane, cyclohexane, cyclo-octane, decalin, benzene, toluene, tetralin and mixtures thereof. It is possible to apply an excess of the (cyclo)alkene or 1-alkyne that is undergoing reaction as a solvent. Other examples of suitable solvents are carbon disulphide, 1,2-dichloroethene, 1,2-dichloroethane, methylene chloride, nitrobenzene, nitroalkanes (nitromethane, nitroethane, 1-nitropropane), chlorobenzene, o-, m- and p-dichlorobenzene, tetrachloroethene, liquid sulphur dioxide, dimethyl sulphoxide, tetramethylene sulphone, sulphuryl chloride fluoride, chloroform, ethyl chloride and dimethyl sulphide; mixtures of two or more of these solvents may be applied, for example of a hydrocarbon and a chlorinated hydrocarbon.

The amount of the Lewis acid used in the process according to the present invention, the temperature and the pressure are not critical. Optimum amounts of Lewis acid depend on the particular catalyst chosen, the type of reaction components, their purity, temperature, desired reaction time, type and amount of solvent (if any) and the like. In general, such amounts of Lewis acid are recommended that one mole of Lewis acid is present per 10 to 100,000 moles of alkene. Although temperatures between −100° and +100° C and even higher can be used, it is one of the special features of the process of the invention that it can be carried out at or near ambient temperature, and accordingly, temperatures between 0° and 100° C, in particular between 0° and 60° C, are preferred. Pressures of up to 100 bar abs. can be used, but the reaction is most conveniently carried out at a pressure between 0.1 and 20 bar abs., in particular at a pressure of about 1 bar abs. or at the pressure of the saturated vapour of the unsaturated material at the reaction temperature concerned, if the latter pressure is higher and 1 bar abs.

The reaction time can be varied widely, for example between 1 minute and 24 hours. Another special feature of the process of the invention is that the reaction is usually completed within 15 minutes.

The process may be effected in the presence or in the absence of molecular oxygen or in the presence of gases such as nitrogen, noble gases or methane, whether or not mixed with oxygen.

After the reaction has been completed, or has been carried out to a desired degree of conversion, it is advantageous to inactivate the Lewis acid before any components of the reaction mixture are isolated. This inactivation of the Lewis acid can be accomplished by addition of a relatively large amount of a compound with an active hydrogen atom, such as water, methanol, ethanol, isopropanol and acetic acid, followed by separation of the precipitate — if any — formed from the liquid.

The products obtained by the process according to the invention can be isolated from the reaction mixture in any convenient manner. By way of example the following methods may be mentioned. If the products do not decompose before or at boiling, they can be isolated from the reaction mixture by fractional distillation. It is also possible to separate the compounds of the reaction mixture by cooling this mixture and removing condensed or crystallized products or by means of gas-chromatographic techniques.

Alkylidenespiro hydrocarbons and polymers thereof can be recovered by, for example, distilling off the volatile products, under reduced pressure, if desired, or by precipitation through addition of non-solvents, for example alcohols, lower carboxylic acids and the like.

The examples further illustrate the invention. The structure of the compounds formed was found by interpretation of their nuclear magnetic resonance spectra.

EXAMPLE 1

A number of experiments in which the alkenes and allenes listed in table A were used as starting materials was carried out as follows. Gaseous allene of atmospheric pressure was conducted into chlorobenzene until saturation at a temperature of 22° C. Then, a quantity of alkene equimolar to the allene was added to the chlorobenzene and subsequently so much of a 4-molar solution of ethylaluminium dichloride in n-hexane was added under stirring that the molar ratio alkene:ethylaluminium dichloride was 50. At the end of the reaction, a small amount of water was added to the reaction mixture to decompose the ethylaluminium dichloride, the liquid was separated by decantation from the precipitate formed by the decomposition, the separated liquid was dried over anhydrous magnesium sulphate and the methylenecyclobutane derivative was isolated from the dried liquid by means of fractional distillation.

Table A shows the reaction times applied, states the methylenecyclobutane(s) formed and presents the yields hereof. A dash indicates that the analysis has not been made. This also holds for Example II.

Table A

| Starting materials | | reaction time, min. | Methylenecyclobutane(s) formed | yield of methylenecyclobutane, % |
| alkene | allene | | | |
|---|---|---|---|---|
| cis-2-butene | allene | 15 | 2,3-dimethylmethylenecyclobutane | 40 |
| trans-2-butene | allene | 15 | 2,3-dimethylmethylenecyclobutane | 15 |
| cis-2-pentene | allene | 15 | 2-ethyl-3-methylmethylenecyclobutane ') 2-methyl-3-ethylmethylenecyclobutane ") | 45 |
| cis-3-hexene | allene | | 2,3-diethylmethylenecyclobutane | — |
| cyclopentene | allene | 15 | 2a,3,4,5,5a-pentahydro-2-methylenecyclobutacyclopentene | 50 |
| cis-2-butene | methylallene | 20 | 2,3-dimethylmethylmethylenecyclobutane | 90 |
| cis-2-butene | 1,1-dimethylallene | 15 | not determined | 35 |
| cis-2-butene | 1,3-dimethylallene | 15 | 2,3,4-trimethylmethylmethylenecyclobutane | 5 |
| 1,4-cyclohexadiene | allene | 10 | 2a,3,6,6a-tetrahydro-2-methylenecyclobutacyclohexene | 45 |
| 1,5-cyclooctadiene | allene | 5 | 2a,3,4,7,8,8a-hexahydro-2-methylenecyclobutacyclooctene | more than 50 |
| 2,3-dimethyl-2-butene | allene | 10 | 2,2,3,3-tetramethylmethylenecyclobutane ''') | more than 90 |
| 2-methyl-2-butene | allene | 10 | 2,3,3-trimethylmethylenecyclobutane and 3,4,4-trimethylmethylenecyclobutane | 15 |
| cis-cyclooctene | allene | 15 | 9-methylene[6,2,0]bicyclodecane | — |
| 2,3,4-trimethyl-2-pentene | allene | less than 10 | 2,2,3-trimethyl-3-isopropyl methylenecyclobutane 2,3,3-trimethyl-2-isopropyl-methylenecyclobutane | more than 90 |
| 2,5-dimethyl-2-hexane | allene | 15 | 2-isobutyl-3,3-dimethylmethylene cyclobutane 2,2-dimethyl-3-isobutyl-methylenecyclobutane | — |

') 45% of the methylenecyclobutanes formed consisted of this compound
") 55% of the methylenecyclobutanes formed consisted of this compound
''') 100% conversion.

The atmospheric boiling points in °C of four of the above-mentioned methylene cyclobutanes are stated below:

| | |
|---|---|
| 2,2,3,3-tetramethylmethylenecyclobutane | 118 |
| 2,3-dimethylmethylenecyclobutane | 68–70 |
| 2,3,3-trimethylmethylenecyclobtuane | 90 |
| 3,4,4-trimethylmethylenecyclobutane | 90 |

| Starting materials | | Alkylidenespiro hydrocarbon formed |
|---|---|---|
| alkene | allene | |
| cis-2-butene | allene | 6,7-dimethyl-2-methylenespiro[3,3]heptane |
| trans-2-butene | allene | 6,7-dimethyl-2-methylenespiro[3,3]heptane |
| cis-2-pentene | allene | 5-ethyl-6-methyl-2-methylenespiro[3,3]heptene and |
| | | 6-ethyl-5-methyl-2-methylenespiro[3,3]heptane |
| cis-3-hexene | allene | 5,6-diethyl-2-methylenespiro[3,3]heptane |
| cyclopentene | allene | spiro[3-methylenecyclobutane-1,1'-1'a,2',3',4',4'a-pentahydrocyclobutacyclopentene] |
| cis-2-butene | methyl-allene | 5,6-dimethyl-2-methylmethylene[3,3]heptane |
| 2,3-dimethyl-2-butene | allene | 5,5,6,6-tetramethyl-2-methylenespiro[3,3]heptane |
| 2,3,4-trimethyl-2-pentene | allene | 5-isopropyl-5,6,6-trimethyl-2-methylene-spiro[3,3]heptane and |
| | | 6-isopropyl-6,7,7-trimethyl-2-methylene-spiro[3,3]heptane |

EXAMPLE II

The following cyclobutacyclobutene derivatives were found in the reaction mixtures:

| Starting materials | | Cyclobutacyclobutene derivative found |
|---|---|---|
| alkene | 1-alkyne | |
| cis-2-butene | 1-butyne | 2a,3-diethyl-4,4a-dihydro-1,2-dihydro-1,2-dimethylcyclobutacyclobutene |
| 2,3-dimethyl-2-butene | propyne | 4,4a-dihydro-2a,3-dimethyl-1,1,2,2-tetramethylcyclobutacyclobutene |
| 2,3-dimethyl-2-butene | 1-butyne | 2a,3-diethyl-4,4a-dihydro-1,1,2,2-tetramethylcyclobutacyclobutene |
| " | 1-pentyne | 4,4a-dihydro-2a,3-n-propyl-1,1,2,2-tetramethyl-cyclobutacyclobutene |
| " | 4-methyl-1-pentyne | 4,4a-dihydro-2a,3-isobutyl-1,1,2,2-tetramethylcyclobutacyclobutene |
| " | 1-heptyne | 4,4a-dihydro-2a,3-n-pentyl-1,1,2,2-tetramethylcyclobutacyclobutene |

Seven experiments in which the 1-alkynes and alkenes listed in table B were used as starting materials were effected as described in example I. The reaction time was 5 to 10 minutes. Table B states the cyclobutene derivative formed and presents the yield thereof.

Table B

| starting materials | | | yield of cyclo- |
|---|---|---|---|
| alkene | 1-alkyne | cyclobutene formed | butene, % |
| cis-2-butene | 1-butyne | 1-ethyl-3,4-dimethylcyclobutene | 5 |
| 1,4-cyclohexadiene | 1-butyne | 2a,3,6,6a-tetrahydro-1-ethylcyclobutacyclohexene ') | 40 |
| 2,3-dimethyl-2-butene | propyne | 1,3,3,4,4-pentamethylcyclobutene | 28,5 |
| 2,3-dimethyl-2-butene | 1-butyne | 1-ethyl-3,3,4,4-tetramethylcyclobutene | 50 |
| " | 1-pentyne | 1-propyl-3,3,4,4-tetramethylcyclobutene | 50 |
| " | 4-methyl-1-pentyne | 1-isobutyl-3,3,4,4-tetramethylcyclobutene | 60 |
| " | 1-heptyne | 1-pentyl-3,3,4,4-tetramethylcyclobutene | 50 |

') 50% conversion

The experiment in which propyne was used also yielded 1.5% of 2,2,3,3-tetrammethylmethylenecyclobutane, formed by isomerization of propyne to allene and reaction of the allene with 2,3-dimethyl-2-butene.

The atmospheric boiling points in °C of two of the above-mentioned cyclobutenes are stated below:

| 1,3,3,4,4-pentamethylcyclobutene | 116 |
|---|---|
| 1-ethyl-3,4-dimethylcyclobutene | 93–95 |

EXAMPLE III 2,3-Dimethyl-2-butene and allene were reacted as described in Example I, with this difference that instead of ethylaluminium dichloride the Lewis acids ferric chloride, aluminium chloride, aluminium bromide, ethylaluminium dichloride, stannic chloride, antimony pentachloride, boron trichloride, boron tribromide and gallium trichloride were each separately tested. The reaction mixture contained 2,2,3,3-tetramethylmethylenecyclobutane. The yields of this compound were 25 and 30% when aluminium bromide and gallium trichloride, respectively, were used.

As an example of the reactions which occur in forming cyclopropanecarboxylic acids the conversion of 2,2,3,3-tetramethylmethylenecyclobutane is given. This compound can be treated with ozone to form 2,2,3,3-tetramethylcyclobutanone, the latter compound can be chlorinated to form 2,2,3,3-tetramethyl-4-chlorocyclobutanone, which can be subjected to ring contraction with formation of 2,2,3,3-tetramethylcyclopropanecarboxylic acid. Certain 2,2,3,3-tetraalykyl-cyclopropanecarboxylates - as stated in British patent specification No. 1,243,858, are biologically active, combining a high insecticidal activity with low mammalian toxicity.

We claim:

1. A process for the preparation of cyclobutene derivatives having the formulas

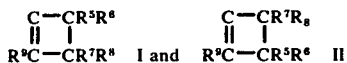  I and  II in which formulas I-II $R^5$ and $R^8$ each individually represents a primary or secondary alkyl group, $R^6$ and $R^7$ a hydrogen atom, a primary or secondary alkyl group, $R^9$ an alkyl group and $R^5$ and $R^6$ each individually represents a hydrogen atom when $R^7$ represents a primary or secondary alkyl group having at least 2 carbon atoms and $R^8$ a primary or secondary alkyl group, which process comprises contacting an alkene having the formula

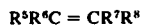  III with a 1-alkyne having the formula

  IV $R^5$, $R^6$, $R^7$, $R^8$ and $R^9$ in the formulas III-IV having the same meanings as in the formulas I-II, in the liquid phase in the presence of a dissolved Lewis acid derived from an element of Group III A of the Periodic Table of the Elements, titanium, tin, antimony, tantalum, rhenium, iron or zinc.

2. A process claimed in claim 1, in which a tetralkylethene is used as the compound of formula III.

3. A process as claimed in claim 2, in which as tetraalkylethene 2,3-dimethyl-2-butene is used.

4. A process as claimed in claim 2, in which as tetraalkylethene 2,3,4-trimethyl-2-pentene is used.

5. A process as claimed in claim 1, in which IV and the alkene having the general formula III are applied in a molar ratio: alkene between 0.1 and 1.5.

6. A process as claimed in claim 1, in which as Lewis acid organometal compound derived from aluminum is used.

7. A process as claimed in claim 6, in which as Lewis acid an alkylhaloaluminium compound is used.

8. A process as claimed in claim 7, in which as alkylhaloaluminium compound a monoalkylaluminium dihalide is used.

9. A process as claimed in claim 8 in which as dihalide a dichloride is used.

10. A process as claimed in claim 9, in which as dichloride ethylaluminium dichloride is used.

11. A process as claimed in claim 1, which is performed in a solvent which does not react with the Lewis acid or the unsaturated compounds present.

12. A process as claimed in claim 1, which is performed at a temperature between 0° and 100° C.

* * * * *

UNITED STATES PATENT AND TRADEMARK OFFICE
CERTIFICATE OF CORRECTION

PATENT NO. : 4,031,152
DATED : June 21, 1977
INVENTOR(S) : JOACHIM H. LUKAS, FRANK BAARDMAN and ADRIAAN P. KOUWENHOVEN It is certified that error appears in the above-identified patent and that said Letters Patent are hereby corrected as shown below:

Claim 5, line 1, after "which" insert --the 1-alkyne having the general formula--.

Claim 5, line 3, change "ratio:alkene" to --ratio 1-alkyne:alkene--.

Signed and Sealed this

Eleventh Day of October 1977

[SEAL]

Attest:

RUTH C. MASON
Attesting Officer

LUTRELLE F. PARKER
Acting Commissioner of Patents and Trademarks